United States Patent [19]
Chambers et al.

[11] Patent Number: 6,048,348
[45] Date of Patent: Apr. 11, 2000

[54] DEFORMABLE INTRAOCULAR LENS INJECTION SYSTEM, AND METHOD THEREOF

[75] Inventors: Thomas J. Chambers, Upland; Vladimir Feingold, Laguna Niguel, both of Calif.

[73] Assignee: STAAR Surgical Company, Inc., Monrovia, Calif.

[21] Appl. No.: 09/050,056

[22] Filed: Mar. 30, 1998

Related U.S. Application Data

[63] Continuation of application No. 08/449,103, May 24, 1995, abandoned, which is a continuation-in-part of application No. 08/197,604, Feb. 17, 1994, Pat. No. 5,499,987, which is a continuation-in-part of application No. 08/221,013, Apr. 17, 1994, Pat. No. 5,494,484, which is a continuation of application No. 07/953,251, Sep. 30, 1992, abandoned.

[51] Int. Cl.[7] .......................................................... A61F 9/00
[52] U.S. Cl. ............................................................. 606/107
[58] Field of Search ................................... 606/107, 106; 604/59, 61; 128/898

[56] References Cited

U.S. PATENT DOCUMENTS

| 4,919,130 | 4/1990 | Stoy et al. ............................. | 606/107 |
| 5,098,439 | 3/1992 | Hill et al. ............................... | 606/107 |
| 5,772,666 | 6/1998 | Feingold et al. ...................... | 606/107 |
| 5,860,984 | 1/1999 | Chambers et al. .................... | 606/107 |

*Primary Examiner*—Michael Buiz
*Assistant Examiner*—Kevin Truong
*Attorney, Agent, or Firm*—Klima & Pezzlo, P.C.

[57] ABSTRACT

A lens injecting device comprising a slidable plunger and means for providing a force in a direction opposite to the direction of advancement of the slidable plunger to provide controlled release of the deformable intraocular lens from the lens injecting device. Further, a method of implantation of a deformable intraocular lens in the eye by forcing the deformable intraocular lens in a folded or condensed configuration through a passageway through an incision in the eye while applying an opposing force to control release of the deformable intraocular lens into the eye.

5 Claims, 3 Drawing Sheets

DEFORMABLE INTRAOCULAR LENS INJECTION SYSTEM, AND METHOD THEREOF

RELATED APPLICATIONS

This is a continuation application of U.S. patent application Ser. No. 08/449,103 filed on May 24, 1995, now abandoned which is a continuation-in-part application of U.S. patent application entitled "DEFORMABLE INTRAOCULAR LENS CARTRIDGE", Ser. No. 08/197,604, filed on Feb. 17, 1994, now U.S. Pat. No. 5,499,987 which is a CIP of U.S. patent application entitled "DEFORMABLE INTRAOCULAR LENS INSERTION SYSTEM", Ser. No. 08/221,013, filed on Apr. 17, 1994, now U.S. Pat. No. 5,494,484 and which is a continuation application of U.S. patent application Ser. No. 07/953,251, filed on Sep. 30, 1992, now abandoned.

FIELD OF THE INVENTION

This invention is directed to a deformable intraocular lens injecting system for surgical implantation of a deformable intraocular lens in the eye. The deformable intraocular lens injecting system preferably comprises a lens injecting device and a lens cartridge. This invention also is directed to a method of using the deformable intraocular lens injecting device according to the present invention, and a method of inserting the deformable intraocular lens into the eye.

BACKGROUND OF THE INVENTION

Presently, deformable intraocular lens are being surgically implanted by various techniques. The majority of these surgical procedures in the United States and abroad involve the use of either 1) surgical forceps; or 2) "shooter" devices for mechanically deforming (e.g., folding, compressing, condensing, rolling, etc.) and manipulating the deformable intraocular lens in a manner to allow insertion through a small incision (2.5 to 3.0 mm) in the eye.

STAAR Surgical Company of Monrovia, Calif., the inventors and originators of the deformable intraocular lens with Dr. Mozzocco, have also been the innovators and suppliers of "shooter" devices to the industry. These "shooter" devices have been widely accepted and currently used by surgeons specializing in the implantation of deformable intraocular lenses.

STAAR Surgical Company informally estimates that approximately fifty (50) percent of all surgical procedures involving the implantation of deformable intraocular lens occur with the use of "shooter" devices.

The original "shooter" devices proposed and designed by Dr. Mozzocco were configured to directly receive a loose unprotected deformable intraocular lens. In such devices, the fully exposed deformable intraocular lens could be potentially damaged while loading the "shooter" device with the deformable intraocular lens. In further developing "shooter" type devices, STAAR Surgical Company made the first "shooter" system comprising an injecting device and a separate one-piece foldable lens cartridge having a lens holding portion connected to a nozzle portion. This development resulted in a "shooter" device that became known in the industry as the "STAAR Shooter". The "STAAR Shooter" became available around 1986, and was supplied on an experimental use basis to surgeons participating in clinical studies seeking approval of implantation of deformable intraocular lens in the human eye by the Food and Drug Administration (FDA), which approval occurred in 1991. An example of a prior art shooter device of STAAR Surgical Company is shown in FIGS. 12 and 13.

The prior art shooter device shown in FIGS. 12 and 13 includes a freely slidable plunger that can be advanced by simply pushing on the one end of the plunger. The slidable plunger includes a tip for contacting with the deformable intraocular lens loaded in a foldable type lens cartridge and forcing the deformable intraocular lens through a nozzle portion of the lens cartridge inserted through a small incision in the eye.

The standard method of use of the prior art shooter device comprises the steps of:

1) loading a deformable intraocular lens into an foldable type lens cartridge opened for receiving the deformable intraocular lens in a flat configuration;

2) closing the foldable type lens cartridge which causes the deformable intraocular lens to fold inside the passageway through the lens cartridge;

3) inserting the loaded lens cartridge into the "STAAR Shooter" device;

4) inserting the tip of the nozzle portion of the lens cartridge through the incision into the eye;

5) advancing the plunger by pushing on the end of the plunger with the thumb while gripping the finger grip connected to the barrel with index finger above and middle finger below so that the tip of the plunger enters into the end of the passageway through the lens cartridge, and then contacts with a trailing end of the deformable intraocular lens; and 6) further advancing the plunger by further pushing on the end of the plunger so that the plunger tip forces the deformable intraocular lens through the passageway in the lens cartridge and out through a tip of the nozzle portion extending through the incision in the eye, thus, allowing the unconstrained deformable intraocular lens to open up (i.e. unfold or decompress) inside the eye.

The manner in which the deformable intraocular lens is released from the tip of the nozzle portion inside the eye can be an important factor with respect to the degree of success of the surgical procedure, and risk of harm or damage to eye tissue during the surgical procedure. In order to increase the degree of success of the surgical procedure and minimize the risk to the patient, it is highly desirable that the deformable intraocular lens is released in a controlled manner, since uncontrolled release of the deformable intraocular lens could cause eye damage. Specifically, due to the resilient nature of the plastic material of the deformable intraocular lens and the plastic material of the nozzle portion of the lens cartridge, the deformable intraocular lens has a tendency to shoot out of the end of the tip of the nozzle portion when uncontrollably released. This phenomenon occurs due to the highly compressed or constrained (i.e. "stressed") configuration of the deformed intraocular lens attempting to expand inside the nozzle portion having resilient walls. When a certain portion of the deformable intraocular lens is extruded or projected a certain critical distance outside the opening of the tip of the nozzle portion, the "stressed" lens will tend to suddenly release and shoot out of the tip of the nozzle portion into the interior of the eye. This phenomenon can result in torn capsular bags and/or damage to tissue in the anterior and posterior chambers in some cases.

In order to control the release of the intraocular lens, various known modifications to the shooters and lens cartridges have been made, and insertion techniques have also been modified. For example, the tip of the nozzle portion can be provided with slits that control the opening and alleviate the expansion force of the folded or compressed intraocular lens exiting the tip of the nozzle portion. Further, the plunger in some shooters is not freely slidable, but instead provided with threaded means for advancing the movement of the plunger. For example, STAAR Surgical Company currently provides a "shooter" under the Model No. MSI-T having a plunger with threaded advancement means allowing for highly controlled fine advancement of the plunger, which provides some controlled release of the deformable intraocular lens.

However, this type of "shooter" having threaded advancing means for controlling the movement of the plunger is not considered desirable by some high volume and high skilled surgeons performing multiple surgical procedures one after another, since any means for restricting the movement of the plunger impedes the surgeon increasing the time for each procedure and potentially limits the maneuverability of the "shooter".

Thus, it is highly desirable to improve both the devices and methods of implanting the deformable intraocular lens in the eye to provide controlled released of the deformable intraocular lens into the eye, and for decreasing the time of the surgical procedure. Also, the ergonomic "feel" for the surgeon using the "shooter" devices can be enhanced by "shooters" according to the present invention tending to increase surgical efficiency and decrease the risk to the patient.

SUMMARY OF THE INVENTION

A first object of the present invention is to provide a deformable intraocular lens injecting system providing controlled release of the deformable intraocular lens into the eye.

A second object of the present invention is to provide a deformable intraocular lens injecting system having means for controlling the release of the deformable intraocular lens into the eye.

A third object of the present invention is to provide a deformable intraocular lens injecting system comprising a nozzle portion having means for controlling the release of the deformable intraocular lens into the eye.

A fourth object of the present invention is to provide a deformable intraocular lens injecting system comprising a lens cartridge having a nozzle portion with means for controlling the release of the deformable intraocular lens into the eye.

A fifth object of the present invention is to provide a deformable intraocular lens injecting system comprising a lens cartridge having a nozzle portion with one or more frangible walls or wall portions for controlling the release of the deformable intraocular lens into the eye.

A sixth object of the present invention is to provide a deformable intraocular lens injecting system comprising a lens injecting device having a movable plunger with means for controlling the release of the deformable intraocular lens into the eye.

A seventh object of the present invention is to provide a deformable intraocular lens injecting system comprising a lens injecting device having a plunger with a spring to control the movement of the plunger and in effect control the release of the deformable intraocular lens into the eye.

An eighth object of the present invention is to provide a deformable intraocular lens injecting system comprising a lens injecting device having a slidable plunger with a spring to control an end portion of the movement of the plunger and in effect control the release of the deformable intraocular lens into the eye.

A ninth object of the present invention is to provide a deformable intraocular lens injecting system comprising a lens injecting device having a slidable plunger with a damper to control the movement of the plunger and in effect control the release of the deformable intraocular lens into the eye.

A tenth object of the present invention is to provide a deformable intraocular lens injecting system comprising a lens injecting device having a slidable plunger with a spring and a damper to control the movement of the plunger and in effect control the release of the deformable intraocular lens into the eye.

An eleventh object of the present invention is providing a method of implantation of a deformable intraocular lens into the eye by forcing the deformable intraocular lens in a folded or condensed configuration through a passageway extending through an incision in the eye while applying an opposite force to control release of the deformable intraocular lens from the passageway into the eye.

The present invention is directed to controllably releasing a folded or condensed deformable intraocular lens into the eye to reduce the risk of harm or damage to a patient's eye during the surgical procedure.

The present invention is directed to apparatus and methods of controlling the release of the advancing folded or condensed deformable intraocular lens by applying a force in a direction opposite to the direction of advancement of the deformable lens when being inserted into the eye. The force can be a constant or variable force, and the force can be selectively applied. These different types of forces can be applied mechanically, fluidly, pneumatically, magnetically, electrically, electromagnetically, combinations of forces, etc. However, mechanically means of applying the force by a spring and/or damper arrangement(s) provide for simple, inexpensive and reliable designs, and currently appear to be the most promising for future developments.

Various configurations of a spring or combination of springs can be applied in the present invention. For example, a coiled spring, cantilever spring, or spring arrangement utilizing the resilient property of the spring's structural configuration and/or the elastic property of the material forming the spring (e.g. plastic resin tubing, longitudinal slits in sides of harder plastic tubing providing a plurality of plate-like springs connected together at ends, plastic or rubber grommets or diaphragms).

The lens injecting device according to the present invention is preferably configured to apply an opposite force to the advancing plunger when the deformable intraocular lens is exiting the nozzle of the lens injecting device to provide controlled release of the deformable intraocular lens into the eye. In a preferred embodiment, the opposite force is applied to the advancing plunger only near the end of its stroke when the deformable intraocular lens is about to exit the tip of the nozzle. This arrangement allows the plunger to freely slide unimpeded most of the distance of its stroke yet provide sufficient back pressure at the end of its stroke to prevent sudden plunger advancement as the intraocular lens exits the nozzle.

DETAILED DESCRIPTION OF PREFERRED EMBODIMENTS

Figure 1:
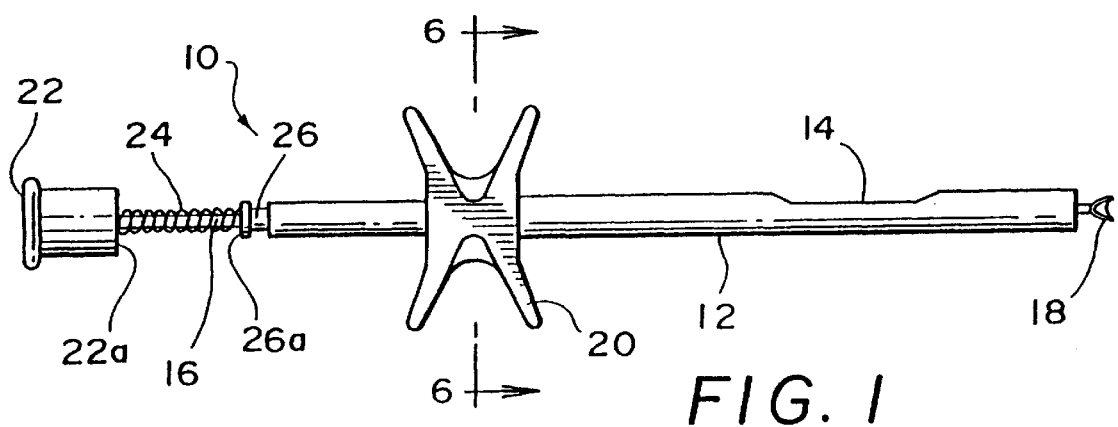
FIG. 1 is a side elevational view of a preferred embodiment of the lens injecting device according to the present invention.
Figure 2:
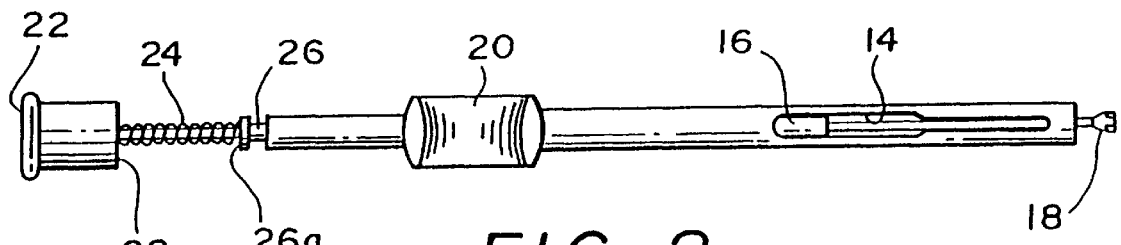
FIG. 2 is a top planar view of the lens injecting device shown in FIG. 1.

A preferred embodiment of a lens injecting device 10 as shown in FIGS. 1 and 2. This lens injecting device is configured for receiving a lens cartridge having a lens holding portion connected to a nozzle portion, and disclosed in the parent applications referred to in the section under related applications.

The lens injecting device 10 comprises a cylindrical barrel 12 having a lens cartridge receiver 14, and a slidable plunger 16 having a plunger tip 18. Further, the cylindrical barrel 12 is provided with a finger grip 20 and the slidable plunger 16 is provided with a thumb grip 22 for manipulating the lens injecting device 10.

Figure 3:
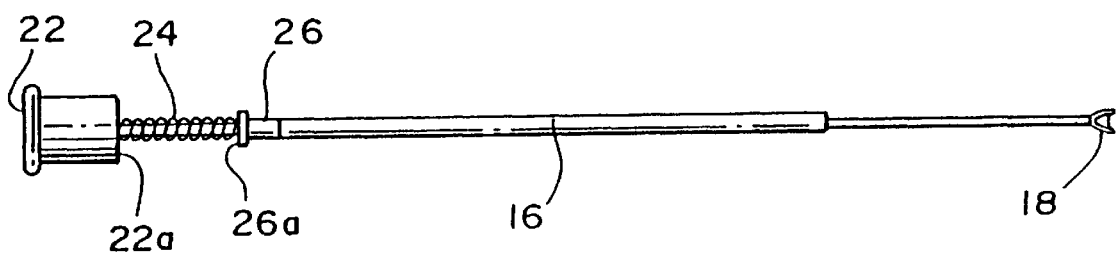
FIG. 3 is a side elevational view of the slidably disposed plunger dissembled from the lens injecting device shown in FIG. 1 to show its detailed structural configuration.
Figure 4:
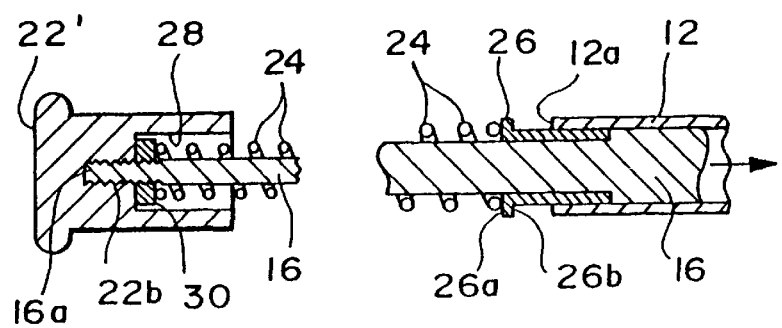
FIG. 4 is a detailed cross-sectional view of an alternative embodiment of the thumb grip having a cylindrical recess to accommodate a fastener having a threaded bore.
Figure 5:
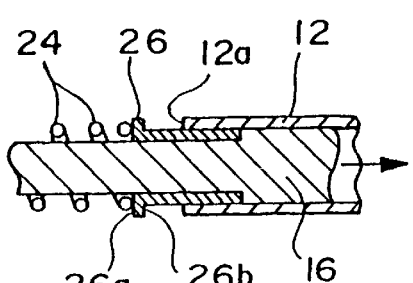
FIG. 5 is a detailed broken away cross-sectional view showing the manner in which the sleeve stop mounted on the slidable plunger engages with an end face of the cylindrical barrel to engage the coiled spring causing a spring force opposite in direction to the advancing slidable plunger.
Figure 6:
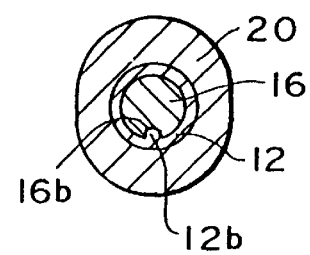
FIG. 6 is a detailed cross-sectional view as indicated in FIG. 1 of the cylindrical barrel and finger grip.

In the preferred embodiment shown in FIGS. 1 and 2, a spring 24 is provided to create a force between the cylindrical barrel 12 and slidable plunger 16. Specifically, the coil type spring 24 is wrapped around a portion of the plunger 16, as indicated on the left-hand side of FIG. 3. Further, the coil type spring 24 extends between the thumb grip 22 and the sleeve stop 26. The face of fastener nut 30 and the end face 26a act as end stops for the spring 24 causing the spring 24 to functionally engage with the slidable plunger 16 when the slidable plunger 16 is moved in a right-ward direction sufficiently to engage an opposite end face 26b of the sleeve stop 26 with the end face 12a of the cylindrical barrel 12, as shown in detail in FIG. 5.

The thumb grip 22 is connected to one end of the slidable plunger 16. For example, the one end of the slidable plunger 16 can be provided with a threaded end portion 16a to be threaded into a threaded bore 22b of the thumb grip 22. In this embodiment of the thumb grip 22', the thumb grip 22' is provided with a cylindrical recess 28 for accommodating a fastener nut 30 threaded onto the end of threaded end portion 16a of the slidable plunger 16. This configuration allows the coil spring 24 to be positioned on the end portion of the slidable plunger 16 and locked in place by the fastener nut 30 prior to the threaded end portion 16a of the slidable plunger 16 being threaded into the threaded bore 22b of the thumb grip 22. This configuration facilitates assembly of the lens injecting device, and more securely restrains the coil spring 24 on the one end of the plunger 16.

The plunger 16 is provided with a lower groove 16b for receiving a inwardly extending protrusion 12b of the cylindrical barrel 12 to provide a locking key way arrangement to prevent relative rotation of the slidable plunger 16 within the cylindrical barrel 12 (i.e., maintains a fixed orientation of the slidable plunger 16 to prevent rotation within the cylindrical barrel 12). Further, the finger grip 20 is securely connected to the cylindrical barrel 12 to prevent any relative movement there between. For example, the finger grip 20 is provided with a through bore that interference fits with the outer surface of a portion of the cylindrical barrel 12.

Figure 7:
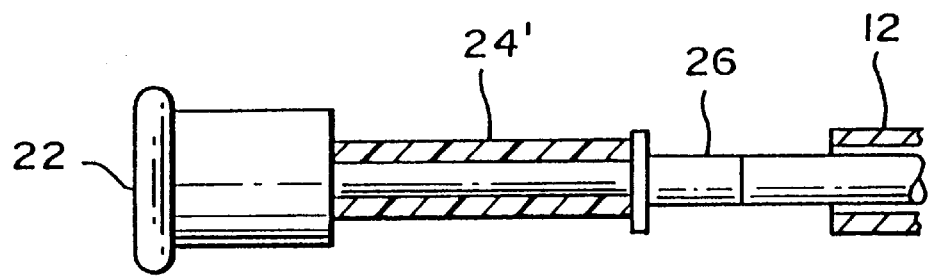
FIG. 7 is a partial broken away view of an alternative spring made of resilient material, e.g. plastic, mounted on the slidable plunger.
Figure 8:
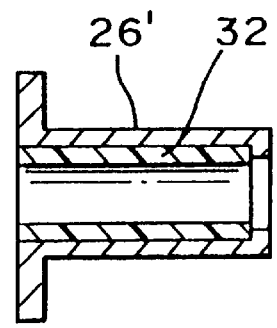
FIG. 8 is a detailed longitudinal cross-sectional view of an alternative sleeve stop having a frictional lining to function as a damper to provide resistance of movement of the advancing slidable plunger.

In an alternative embodiment as shown in FIG. 7, the coil spring 24 is replaced with a section of resilient rubber or plastic tubing 24' performing the function of a spring due to the resilient nature of the material making up the section of tubing. As a further alternative, as shown in FIG. 8, a sleeve stop 26' having a frictional lining 32 (e.g., synthetic plastic, ceramic, metal, glass, etc.) provides somewhat of a friction fit with an outer surface of the plunger to function as a damper resisting the forward movement of the slidable plunger to control release of the deformable intraocular lens from the tip of the nozzle portion of the lens cartridge.

The examples of springs and dampers discussed above are only illustrative examples embodying the concepts of the present invention, however, other types of springs (e.g., cantilever type) and/or dampers (e.g., viscous fluid medium between plunger and cylindrical barrel) can be provided as alternatives to the preferred embodiment shown.

Figure 9:
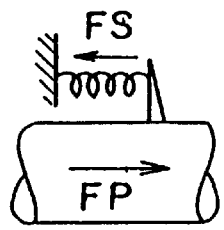
FIG. 9 is a diagrammatic view of a slidable plunger provided with a spring for applying force in an opposite direction of advancement of the slidable plunger.
Figure 10:
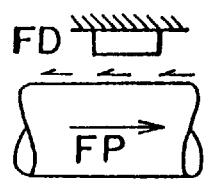
FIG. 10 is a diagrammatic view of a slidable plunger provided with a damper to function as a damper to provide resistance of movement of the advancing slidable plunger.
Figure 11:
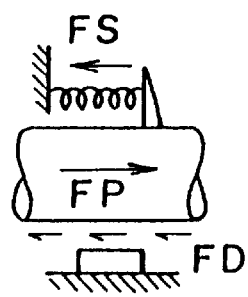
FIG. 11 is a diagrammatic view of a slidable plunger provided with both a spring and damper.
Figure 12:
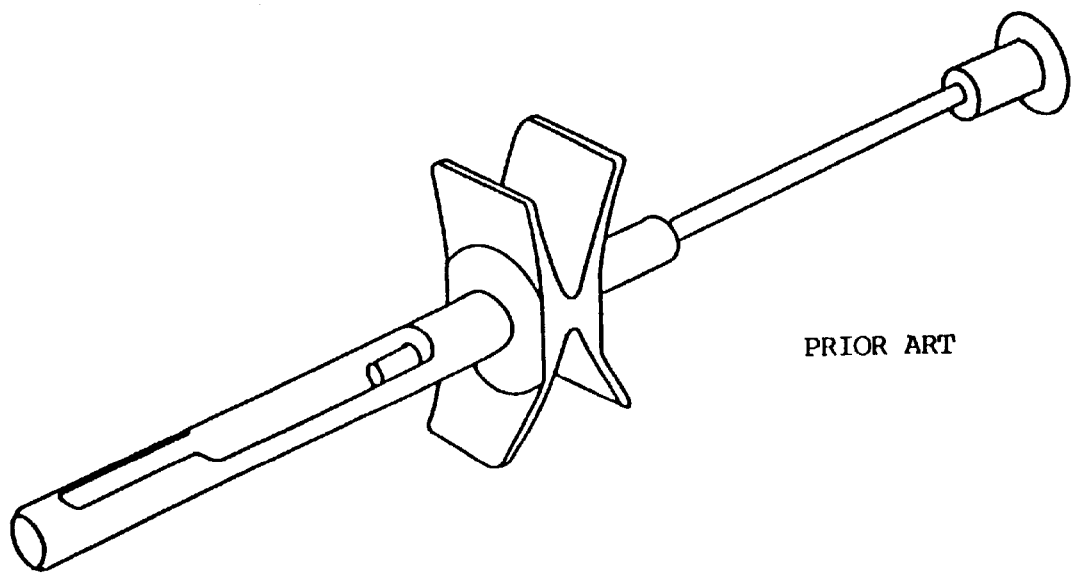
FIG. 12 is a perspective view of a prior art embodiment of a shooter device of STAAR Surgical Company of Monrovia, Calif.
Figure 13:
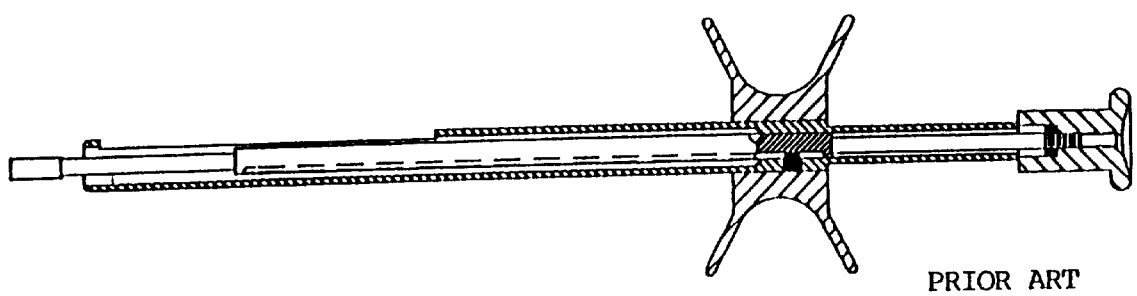
FIG. 13 is a longitudinal cross-sectional view of the prior art shooter device shown in FIG. 13.

FIGS. 9 through 11 schematically illustrate applying a spring force, applying a damping resistance force, and combining both spring force and damping resistance force, respectively, for controlling the forward movement of the slidable plunger and for controlling the release of the deformable intraocular lens from the nozzle of the injecting device.

The method according to the present invention involves providing either a spring force, or damping resistance force against a force for inserting the deformable intraocular lens through a passageway of a device for inserting a deformable intraocular lens through an incision in the eye. The spring force and/or damping resistance force control the forward advance of the deformable intraocular lens through the passageway for controlling the release thereof into the eye.

What is claimed is:

1. A method of inserting a deformable intraocular lens through a small incision in the eye, comprising the steps of:

loading the deformable intraocular lens into a lens injecting device having a lens delivery passageway configured to extend through the incision in the eye, said lens injecting device including a plunger slidably disposed within said lens delivery passageway;

forcing the deformable intraocular lens through said lens delivery passageway with a tip of said plunger; and providing a damping resistance force between said plunger and said lens delivery passageway in a direction opposite to a direction of movement of said plunger when said lens injecting device is being operated by a user to control release of the deformable intraocular lens from an exit end of said lens delivery passageway into the eye.

2. The method of claim 1, wherein said damping resistance force is substantially a constant resistance force.

3. The method of claim 1, wherein said damping resistance force is a variable resistance force.

4. The method of claim 1, including a step of providing a spring resistance force between said plunger and said lens delivery passageway in a direction opposite to the direction of movement of said plunger.

5. The method of claim 4, wherein the resistance increases in the direction of movement of the deformable intraocular lens into the eye.

* * * * *